United States Patent [19]

Lang

[11] Patent Number: 4,779,352
[45] Date of Patent: Oct. 25, 1988

[54] METHOD AND APPARATUS FOR MEASURING COATING LAYER THICKNESSES ON MOTOR VEHICLE BODIES

[75] Inventor: Hans Lang, Dusseldorf, Fed. Rep. of Germany

[73] Assignee: Ford Motor Company, Dearborn, Mich.

[21] Appl. No.: 66,791

[22] Filed: Jun. 25, 1987

[30] Foreign Application Priority Data

Jul. 5, 1986 [DE] Fed. Rep. of Germany ....... 3622708

[51] Int. Cl.4 .............................................. G01B 7/06
[52] U.S. Cl. .................................. 33/169 F; 324/229
[58] Field of Search ............ 33/169 F, 169 R, 172 E; 324/230, 229, 231; 73/150 R

[56] References Cited

FOREIGN PATENT DOCUMENTS 2742058  3/1979  Fed. Rep. of Germany .

OTHER PUBLICATIONS

"Automobil Revue", No. 13, p. 51, dated Mar. 27, 1986.

Primary Examiner—Harry N. Haroian
Attorney, Agent, or Firm—Peter D. McDermott; Roger L. May

[57] ABSTRACT

A method and an apparatus are provided for testing final coating layer thicknesses on motor vehicle bodies by means of measuring probes moved along a body by way of automatic manipulators. A measuring probe (20), disposed in a guide member suspended on gimbals, is attached to the surface of the body by means of a suction cup (15), an inner stop ring (16) and a spring (21) which cooperate to ensure that the measuring probe is applied with a specific pressure.

6 Claims, 2 Drawing Sheets

METHOD AND APPARATUS FOR MEASURING COATING LAYER THICKNESSES ON MOTOR VEHICLE BODIES

INTRODUCTION

The present invention relates to a method and an apparatus for measuring coating layer thicknesses on motor vehicle bodies. More specifically, the invention relates to a method and apparatus for measuring such coating layer thicknesses while the motor vehicle bodies are moving.

BACKGROUND

German Offenlegungsschrift (Laid-Open Specification) No. 27 42 058 discloses an apparatus for applying measurement value sensors and measurement electrodes on surfaces. The apparatus comprises a suction cup which surrounds a measuring probe and which is acted upon with vacuum. While the suction cup and measuring probe are adapted for use on skin surfaces, the apparatus is limited in its usefulness in that it is not provided with any means for vertically orientating and pressing the measuring probe with a predetermined pressure.

A method of testing the final coatings on motor vehicle bodies is known from the journal "Automobil Revue" No. 13 of 27-3-1986, page 51, in which a measuring probe is guided along a body by way of automatic manipulators. The automatic manipulator required for this must be precisely controlled by way of suitable sensors, in order that it can guide the measuring sensor along the curved profile of a body. This requires a relatively complicated automatic manipulator with a very expensive sensor control device. In addition, the body must be held stationary during the measuring procedure, so that this measurement cannot be carried out in the normal production procedure of motor vehicle bodywork manufacture.

The object of the invention is to provide a method of measuring coating layer thicknesses on motor vehicle bodies in such a way the measurement can be carried out by means of simple automatic manipulators while the vehicle bodies are moving.

SUMMARY OF THE INVENTION

According to the present invention a method is provided for determining the thickness of a coating layer on the surface of a motor vehicle body by means of a measuring probe of any known type. The method is characterized by the following method steps:

(a) moving the measuring probe, disposed in a guide means which is suspended on gimbals, approximately at right angles (i.e., normal) to such surface of the moving body;
(b) placing the measuring probe upon the surface of the body with a specific pressure;
(c) moving the measuring probe in synchrony with the body for a specific period of time; and
(d) raising the measuring probe and moving it back to its initial position.

According to a second aspect of the present invention an apparatus is provided for carrying out the foregoing method. Specifically, an apparatus is provided for determining a coating layer thickness on a surface of a moving motor vehicle body, which apparatus comprises an automatic manipulator and a measuring probe arrangement received by the automatic manipulator. The measuring probe arrangement is moveable along three axes X, Y and Z, as further defined below. The measuring probe arrangement, specifically, is mounted to a displacement device which is selectively moveable in a direction approximately normal to the aforesaid surface of the moving body. Tee measuring probe arrangement comprises a guide portion suspended in gimbals and a sleeve portion received by and axially displaceable within and relative to the guide portion against the force of a spring. The sleeve portion has at its front end a suction cup, open to the aforesaid body surface and having an inner stop ring adapted to contact such surface and to stop axial movement of the measuring probe arrangement toward the surface at a fixed relative position. A measuring probe of the measuring probe arrangement extends coaxially with the stop ring and is axially displaceable within the aforesaid sleeve portion against the force of a second spring. A vacuum line communicates with the suction cup to create a vacuum therein to affix same to the aforesaid body surface, whereby the measuring probe arrangement is held to the surface and the measuring probe thereof is placed upon the surface with a specific, preselected pressure. The measuring probe arrangement further comprises a sensor adapted to sense movement of the guide portion to a preselected limit and to actuate the aforesaid displacement device of the automatic manipulators.

It is a significant advantage of the present invention that a complicated apparatus for synchronization between the movement of a measuring device and the movement of the vehicle body can be dispensed with. The measuring probe of the invention is disposed in a guide means which is suspended on gimbals, is moved approximately at right angles to the surface of a moving body, is placed vertically upon the surface of the body with a specific pressure, is held there for a period of time while jointly moving therewith, and is then raised and moved back to its initial position.

In the following discussion of the invention, reference will be made to axes X, Y and Z. Axes X and Y will refer to direction of movement at right angles to each other and parallel to the plane of a surface whose coating layer thickness is being measured. Axis X, specifically, refers to a direction transverse to the direction of movement of the surface. Thus, axis Y is parallel to the direction of movement. Axis Z refers to a direction of movement at right angles to X and Y and normal to the plane of such surface.

According to a significant feature of the present invention, an automatic manipulator receives a measuring probe arrangement so as to be movable along three axes X, Y and Z. The measuring probe arrangement is disposed in a guide means suspended on gimbals and is guided in the Z-direction, i.e., approximately at right angles to the surface of a moving bodywork. The measuring probe arrangement is moved in the Z-direction to such surface and there is applied in a yielding manner with an inner stop ring by way of a sleeve portion axially displaceable in the guide means against the force of a spring. A suction cup is secured to the sleeve portion. The measuring probe is directed by the inner stop ring at right angles to the surface of the body and is held on the surface of the body by vacuum communicated to the suction cup. Since the measuring probe is axially displaceable in the sleeve portion against the bias of a spring, it is consistently pressed with a predetermined pressure upon the surface of the body. Consequently, a reliable measurement of the coating layer thickness along a line of predetermined measurement points is achieved. It is a significant advantage of the invention that reliable thickness measurements are achieved with a relatively simple and inexpensive structural design. In addition, the invention provides such reliable measurements on a moving surface. That is, the movement of the vehicle bodywork has little or no effect upon the accuracy of the measurements.

DESCRIPTION OF THE DRAWINGS

The invention is explained in greater detail with reference to an embodiment illustrated in the accompanying drawings, in which.

DETAILED DESCRIPTION OF THE INVENTION

Figure 1:
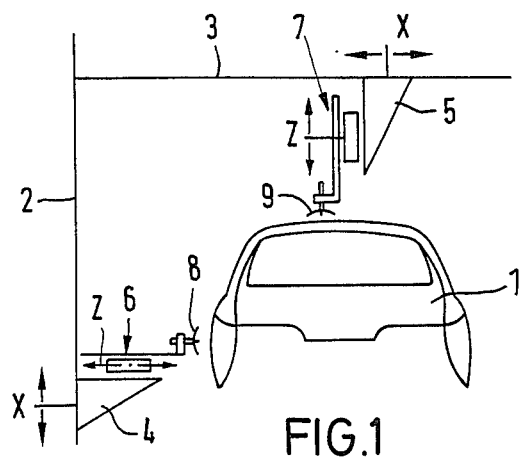
FIG. 1 is a diagrammatic front view of an apparatus according to the invention.
Figure 2:
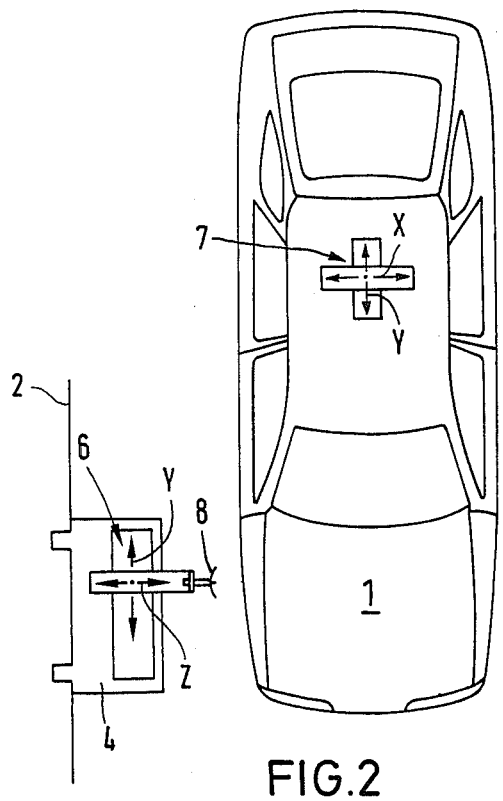
FIG. 2 is a diagrammatic plan view of an apparatus according to the invention.

A body 1 of a motor vehicle, which is moved in a longitudinal direction by way of a conveying means (not shown) known per se is illustrated diagrammatically in FIGS. 1 and 2. Brackets 4 and 5 are mounted on a side wall 2 and on a ceiling 3, respectively, adjacent the path of movement of the body. These brackets support simple automatic manipulators 6 and 7, respectively, which comprise elements which are movable in the X-direction, i.e. transversely to the direction of movement of the body 1, in the Y-direction, i.e. parallel to the direction of movement of the body 1, and in the Z-direction, i.e. in a direction normal to the surface of the body 1. Measuring probe devices 8 and 9, the design of which is explained in greater detail in conjunction with FIG. 3, each is mounted on a displacement device, i.e. the element of the automatic manipulators 6 and 7 movable in the Z-direction.

Figure 3:
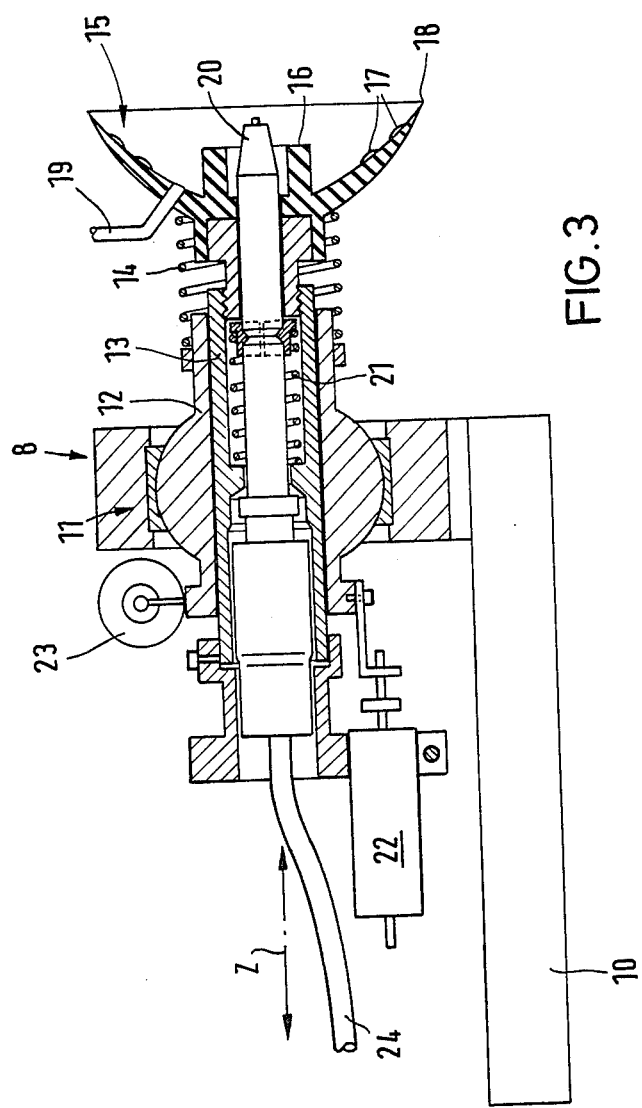
FIG. 3 is a vertical section through the measuring probe arrangement according to the invention, disposed on the Z-axis of the automatic manipulators.

FIG. 3 is a vertical section through the Z-axis of an automatic manipulator, of which only the displacement device 10 for the Z-axis is indicated. A measuring probe arrangement 8 is secured to the displacement device 10. The measuring probe arrangement 8 comprises a guide member 12, which is suspended on gimbals in a ball-and-socket joint 11 and in which a sleeve portion 13 is arranged so as to be axially displaceable against the force of a spring 14. At its front end the sleeve portion 13 is provided with a suction cup 15 and an inner stop ring 16, stop pegs 17 and an outer suction lip 18. Vacuum can be drawn in the interior of the suction cup 15 by way of a vacuum line 19.

Inside the suction cup 15 and inside the inner stop ring 16 a measuring probe 20 is disposed in the sleeve portion 13 so as to be axially displaceable against the force of a spring 21. The measurement values detected by the measuring probe 20 are fed to an evaluation or display device by way of a probe cable 24.

Two path sensors 22 and 23 engage the guide member 12 by way of corresponding rod systems. At the start of a measurement procedure the measuring probe arrangement 8 is moved rapidly by way of the displacement device 10 approximately at right angles to the surface of the body. As soon as the suction cup 15 meets the surface of the body (not shown) it abuts by way of the stop pegs 17 and the measuring probe arrangement 8 is orientated by the gimbal suspension by way of the ball-and-socket joint 11 at right angles to the surface of the body. As soon as the measuring probe arrangement 8 meets the surface of a body, path sensor 22 is thereby actuated to switch off the displacement device 10. The abutment of the suction cup 15 on the surface of the body leads, however, since the body is moving, to an entrainment of the suction cup 15. This movement, in the direction of the Y-axis, is detected by the path sensor 23 which is thereby actuated to switch off the displacement device of the automatic manipulator in the direction of the Y-axis and causes a vacuum to be drawn through vacuum line 19. As a result, the suction cup 15 is brought close to the surface of the body and holds the entire measuring probe arrangement 8 immovably against the moving body and entrains it.

The suction of suction cup 15 on the surface of the body causes inner stop ring 16 to be brought to the body surface. The measuring probe 20 disposed inside the inner stop ring 16 is pressed back axially against the force of its spring 21. This ensures the constant pressure required for a precise measurement. As soon as the measurement result has been passed to a signal receiving means, such as a measurement or display device, by way of the probe cable 24, the measurement or display device actuates a vacuum termination means to discontinue the vacuum drawn within suction cup 15. Suction cup 15 then is lifted off the surface of the body. Path sensors 22 and 23 again actuate the displacement devices of the automatic manipulators, which first remove the measuring probe arrangement 8 from the body and then return it to its initial position in the direction opposite to the direction of movement of the body.

By virtue of the fact that the measuring probe is held immovably against the surface of the body by way of the suction cup during the measurement procedure, a complicated synchronization between the movement of the body and a movement of the automatic manipulators can be dispensed with during this period. As a result, complicated apparatus otherwise required for independently maintaining such synchronization is avoided. In the present invention the movement which must be performed by the automatic manipulators consist only of rapidly bringing the measuring probe arrangement to the surface of the body, while after the attachment of the suction cup the displacement devices of the automatic manipulators are held freely running, released by the movement sensors for the Z- and Y-direction and are actuated again only after the measuring probe arrangement has been lifted, in order to move the measuring probe arrangement away from the body and back into its initial position.

On account of the method and the apparatus of the invention, trouble-free measurement of the coating layer thickness on moving motor vehicle bodies is possible. Thus, measuring devices can, where necessary, be mounted directly at locations on the production line at which the body is moved out of one of the many coating application areas.

It should be understood that various modifications to the inventive concepts set forth above will be apparent to those skilled in the art and all such modifications are included within the spirit and scope of the invention.

I claim:

1. An apparatus for determining a coating layer thickness on a surface of a moving motor vehicle body, said apparatus comprising an automatic manipulator and a measuring probe arrangement mounted to a displacement device of said automatic manipulator and movable along three axes X, Y and Z, said displacement device being selectively movable in a direction approximately normal to said surface, said measuring probe arrangement comprising:
- a guide portion suspended on gimbals;
- a sleeve portion axially displaceable within and relative to said guide portion against the force of a spring, said sleeve portion having at its front end a suction cup, open to said surface, with an inner stop ring adapted to contact said surface and to stop axial movement of said measuring probe arrangement toward said surface;
- a measuring probe extending coaxially with said stop ring and being axially displaceable within said sleeve portion against the force of a second spring;
- a vacuum line communicating with said suction cup to draw a vacuum therein; and
- a sensor adapted to sense movement of said guide portion to a preselected limit and to actuate said displacement device of said automatic manipulator.

2. The apparatus of claim 1 further comprising a second sensor adapted to sense movement of said guide portion to a preselected limit and to actuate a second displacement device of said automatic manipulator, which second displacement device is adapted to move said measuring probe arrangement in a direct at right angles to that of said displacement device.

3. The apparatus of claim 1 further comprising a probe cable connected to said measuring probe and adapted to communicate signals generated by said measuring probe.

4. The apparatus of claim 1 further comprising a second automatic manipulator and a second measuring probe arrangement mounted to said second automatic manipulator and adapted to determine a coating layer thickness on a second surface of said moving motor vehicle body.

5. The apparatus of claim 1 further comprising a signal receiving means adapted to receive a signal from said measuring probe, and a vacuum termination means, said signal receiving means being adapted to actuate said vacuum termination means to discontinue vacuum being drawn within said suction cup.

6. A method of determining a coating layer thickness on a moving motor vehicle body by means of a measuring probe, characterized by the following method steps:
- (a) moving said measuring probe, disposed in a guide means which is suspended on gimbals, approximately at right angles to a surface of said moving body;
- (b) placing said measuring probe upon said surface of said body with a specific pressure;
- (c) moving said measuring probe in synchrony with said body for a specific period of time; and
- (d) raising and moving said measuring probe back to its initial position.

* * * * *